US00PP20244P2

(12) United States Plant Patent
Radler

(10) Patent No.: US PP20,244 P2
(45) Date of Patent: Sep. 1, 2009

(54) SHRUB ROSE PLANT NAMED 'RADLIV'

(50) Latin Name: *Rosa hybrida*
Varietal Denomination: Radliv

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/222,518

(22) Filed: Aug. 11, 2008

(51) Int. Cl.
*A01H 5/00* (2006.01)

(52) U.S. Cl. ..... Plt./108
(58) Field of Classification Search ..... Plt./108
See application file for complete search history.

*Primary Examiner*—Kent L Bell
(74) *Attorney, Agent, or Firm*—Buchanan Ingersoll & Rooney PC

(57) ABSTRACT

A new and distinct shrub rose plant is provided that abundantly and substantially continuously forms attractive semi-double blossoms that are dark red in coloration. The plant exhibits vigorous vegetation and a bushy, fairly loose and open growth habit. The foliage is dark green with a matte finish. A faint sweet fragrance is provided by the blossoms. The plant is well suited for growing as attractive ornamentation in parks and gardens.

1 Drawing Sheet

Botanical/commercial classification: *Rosa hybrida*/shrub rose plant.

Varietal denomination: cv. 'Radliv'.

SUMMARY OF THE INVENTION

The new variety of *Rosa hybrida* shrub rose plant of the present invention was created at Greenfield, Wis., U.S.A., by artificial pollination wherein two parents were crossed which previously had been studied in the hope that they would contribute the desired characteristics. The female parent (i.e., the seed parent) was the 'Radvel' variety (non-patented in the United States). The male parent (i.e., the pollen parent) of the new variety was the 'Country Dancer' variety (non-patented in the United States). The parentage of the new variety can be summarized as follows:

'Radvel'×'Country Dancer'.

The seeds resulting from the above pollination were sown and small plants were obtained which were physically and biologically different from each other. Selective study resulted in the identification of a single plant of the new variety.

It was found that the new shrub rose plant of the present invention possesses the following combination of characteristics:

(a) abundantly and substantially continuously forms attractive semi-double blossoms that are dark red in coloration,
(b) exhibits a bushy, fairly loose and open growth habit,
(c) forms vigorous vegetation,
(d) forms attractive dark green foliage with a matte finish, and
(e) is well suited for providing attractive ornamentation in the landscape.

A new rose variety is provided which bears attractive dark red blossoms combined with substantially continuous blooming. The long blooming cycle of the new variety is generally comparable to that of the KNOCK OUT® family of rose plants which includes the 'Radrazz' variety (U.S. Plant Pat. No. 11,836), 'Radyod' variety (U.S. Plant Pat. No. 14,700, 'Radcon' variety (U.S. Plant Pat. No. 15,070, 'Radtko' variety (U.S. Plant Pat. No. 16,202), 'Radcor' variety (U.S. Plant Pat. No. 17,346), 'Radtkopink' (U.S. Plant Pat. No. 18,507) and 'Radsunny' (U.S. Plant Pat. No. 18,562).

The new variety well meets the needs of the horticultural industry. It can be grown to advantage as ornamentation in parks, gardens, public areas, and in residential settings. The new variety is particularly well suited for providing attractive ornamentation in the landscape. The dark red blossoms contrast nicely with the matte dark green foliage.

The new variety of the present invention can be readily distinguished from its ancestors. More specifically, unlike the new variety the 'Radvel' variety forms blossoms having only 5 or 6 petals and smaller foliage, and the 'Country Dancer' variety displays deep pink double blossoms that commonly display approximately 38 petals. The new variety of the present invention also can be readily distinguished from the 'Radrazz' variety in several respects including blossom coloration and a greater susceptibility to Black Spot. The blossoms of the 'Radrazz' variety are cherry red and are almost florescent when present in full sun. The dark red blossoms of the new variety are near velvet in appearance. The exceptional resistance to Black Spot of the 'Radrazz' variety particularly when grown on the East Coast of the United States commonly exceeds that of the new variety. While the new variety displays tolerance to Black Spot, it may eventually succumb to the disease during mid-summer as evidenced by the yellowing of the lower leaves and other signs of Black Spot.

The characteristics of the new variety have been found at Waso, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radliv' and will be marketed in the United States under the MIDWEST LIVING trademark.

BRIEF DESCRIPTION OF THE PHOTOGRAPH

The accompanying photographs show, as nearly true as it is reasonably possible to make the same in color illustrations of this character, typical specimens of the new variety. The illustrated rose plants of the new variety were approximately four years of age and were observed during July while growing outdoors near West Grove, Pa., U.S.A.

DETAILED DESCRIPTION

Figure 1:
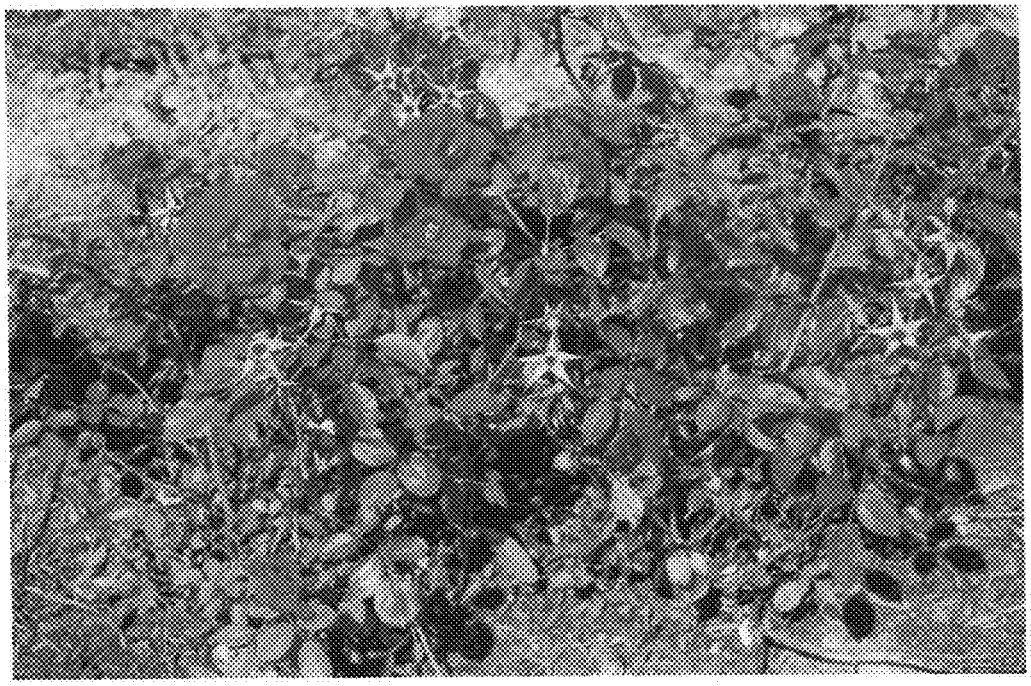
FIG. 1 shows a pair of typical flowering plants.
Figure 2:
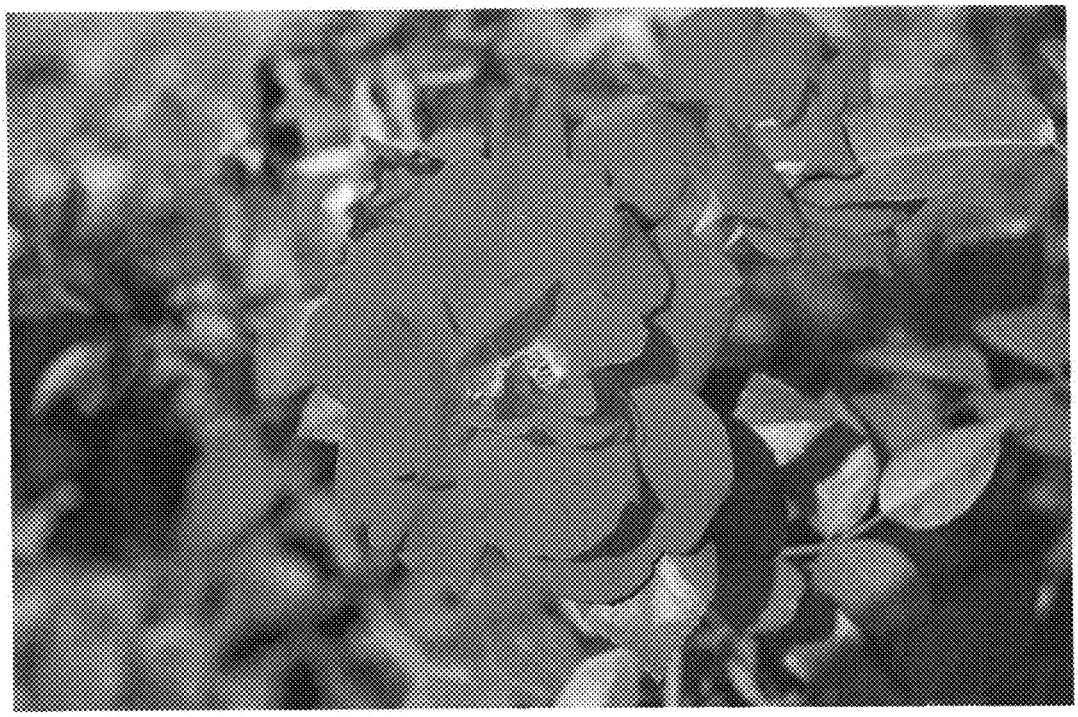
FIG. 2 shows a close view of typical dark red blossoms and the dark green foliage which displays a matte finish.

The chart used in the identification of colors is that of The Royal Horticultural Society (R.H.S. Colour Chart), London, England. The description is based on the observation of two-year-old specimens of the new variety during July while growing outdoors near West Grove, Pa., U.S.A.

Class: Landscape Shrub.

Plant:

*Height.*—Approximately 3.5 to 4 feet on average at the end of the growing season.

*Width.*—Approximately 3.5 to 4 feet on average at the end of one growing season.

*Habit.*—Bushy, fairly loose and open.

Branches:

*Color.*—Young stems: near Yellow-Green Group 146B. Adult wood: Yellow-Green Group 147B.

*Thorns.*—Size: approximately 5 mm in length, approximately 4 mm in width at the base, less than 1 mm in width at the apex, and commonly near Red Group 37C in coloration.

Leaves:

*Leaflets.*—Number mostly 5 and 7. Length: approximately 4 cm on average for a terminal leaflet, and approximately 3 cm on average for a lower leaflet. Width: approximately 2.5 cm on average at the widest point for a terminal leaflet, and approximately 1.5 cm on average at the widest point for a lower leaflet. Shape: ovate with a rounded base and an acuminate tip. Margins: double serrate. Texture: smooth on both surfaces, leathery, and with a coarse midrib on the under surface. Overall appearance: attractive dark green matte leaves. Color (young foliage): upper surface: commonly between Greyed-Orange Group 173A and Yellow-Green Group 152A. Under surface: commonly near Greyed-Orange Group 176B. Color (adult foliage): upper surface: commonly near Green Group 137B. Under surface: commonly near Yellow-Green Group 146C.

*Stipules.*—Length: approximately 1 cm on average. Texture: smooth on both surfaces. Color: near Yellow-Green Group 144A.

*Petioles.*—Upper surface: smooth. Under surface: somewhat roughened with a few prickles commonly less than 2 mm in length.

Inflorescence:

*Number of flowers.*—Commonly approximately 5 blooms on average in a cluster.

*Peduncle.*—Near Yellow-Green Group 145A in coloration, commonly approximately 9 mm in length, and approximately 10 mm in diameter.

*Sepals.*—Upper surface: smooth and glaucous, and commonly near Yellow-Green Group 146D in coloration. Under surface: smooth and near Yellow-Green Group 146C in coloration. Size: commonly approximately 2.8 cm in length on average, and approximately 0.7 cm in width at the base. Number: five.

*Buds.*—Shape: pointed at tip. Length: approximately 2.5 cm on average as the calyx breaks. Diameter: approximately 1.5 cm as the calyx breaks. Color: Red Group 53A.

*Flower.*—Form: semi-double. Shape: cuplike, semi-double and informal. Diameter: approximately 7 cm on average when fully open. Color (when opening begins): upper surface: near Red Group 46A. under surface: near Red Group 46A. Color (at end of blooming): upper surface: near Red Group 46A. under surface: near Red Group 46A. Fragrance: faint sweet scent. Petal number: commonly approximately 10 to 12 on average. Petaloids: commonly 5 to 7 on average. Petal shape: commonly somewhat reflexed under to form a pointed tip. Petal drop: the petals commonly drop cleanly at full maturity. Stamen: approximately 35 on average, and regularly arranged about the pistils. Anthers: near Greyed-Orange Group 176B in coloration. Filaments: approximately 5 mm in length, and near Yellow Group 12C in coloration. Pistils: separate and free. Styles: commonly approximately 4 mm in length, and near Red Group 53B in coloration. Stigmas: approximately 1 mm in diameter, and near Orange Group 26B in coloration.

Development:

*Vegetation.*—Vigorous and strong.

*Blossoming.*—Abundant and substantially continuous during the growing season.

*Resistance to insects.*—Has proven to be resistant to leafhoppers and midge during observations to date.

*Tolerance to disease.*—Some tolerance to Black Spot has been displayed, and commonly less resistance to Black Spot than the 'Radrazz' variety.

*Hardiness.*—During observations to date the plant has proven to be hardy to U.S.D.A. Hardiness Zone No. 5, and to U.S.D.A. Zone No. 4 with winter protection.

*Formation of hips/seeds.*—None have been observed during observations to date.

I claim:

1. A new and distinct shrub rose plant characterized by the following combination of characteristics:

(a) abundantly and substantially continuously forms attractive semi-double blossoms that are dark red in coloration, (b) exhibits bushy, fairly loose and open growth habit, (c) forms vigorous vegetation, (d) forms attractive dark green foliage with a matte finish, and (e) is well suited for providing attractive ornamentation in the landscape;

substantially as herein shown and described.

* * * * *